United States Patent [19]

Chamuel

[11] Patent Number: 5,053,017
[45] Date of Patent: Oct. 1, 1991

[54] HYPODERMIC NEEDLE SAFETY CLIP

[76] Inventor: Steven R. Chamuel, 26 Murray St., Peabody, Mass. 01960

[21] Appl. No.: 487,457

[22] Filed: Feb. 28, 1990

[51] Int. Cl.⁵ .............................................. A61M 5/32
[52] U.S. Cl. ...................................... 604/192; 604/263
[58] Field of Search ............... 604/192, 198, 199, 110, 604/263, 264

[56] References Cited

U.S. PATENT DOCUMENTS

| | | | |
|---|---|---|---|
| 1,115,561 | 11/1914 | Northey | 604/192 |
| 1,518,531 | 12/1924 | Lung | 604/272 |
| 2,854,976 | 10/1958 | Heydrich | 604/192 |
| 3,884,230 | 5/1975 | Wulff | 128/221 |
| 3,890,971 | 6/1975 | Leeson et al. | 128/218 |
| 3,904,033 | 9/1975 | Haerr | 604/263 |
| 3,976,070 | 8/1976 | Dumont | 128/221 |
| 4,026,287 | 5/1977 | Haller | 128/215 |
| 4,258,713 | 3/1981 | Wardlaw | 128/218 |
| 4,266,543 | 5/1981 | Blum | 128/218 |
| 4,392,859 | 7/1983 | Dent | 604/198 |
| 4,425,120 | 1/1984 | Sampson et al. | 604/198 |
| 4,482,348 | 11/1984 | Dent | 604/198 |
| 4,507,118 | 3/1985 | Dent | 604/198 |
| 4,573,976 | 3/1986 | Sampson et al. | 604/198 |
| 4,631,057 | 12/1986 | Mitchell | 604/198 |
| 4,639,249 | 1/1987 | Larson | 604/198 |
| 4,643,199 | 2/1987 | Jennings, Jr. et al. | 128/763 |
| 4,643,200 | 2/1987 | Jennings, Jr. | 128/763 |
| 4,664,654 | 5/1987 | Strauss | 604/198 |
| 4,676,783 | 6/1987 | Jagger et al. | 604/171 |
| 4,681,567 | 7/1987 | Masters et al. | 604/198 |
| 4,693,708 | 9/1987 | Wanderer et al. | 604/198 |
| 4,695,274 | 9/1987 | Fox | 604/198 |
| 4,723,943 | 2/1988 | Spencer | 604/198 |
| 4,728,320 | 3/1988 | Chen | 604/192 |
| 4,731,059 | 3/1988 | Wanderer et al. | 604/192 |
| 4,737,144 | 4/1988 | Choksi | 604/198 |
| 4,738,663 | 4/1988 | Bogan | 604/198 |
| 4,743,233 | 5/1988 | Schneider | 604/192 |
| 4,747,836 | 5/1988 | Luther | 604/198 |
| 4,747,837 | 5/1988 | Hauck | 604/198 |
| 4,748,231 | 7/1988 | Haber et al. | 604/198 |
| 4,752,290 | 6/1988 | Schramm | 604/198 |
| 4,770,655 | 9/1988 | Haber et al. | 604/110 |
| 4,772,272 | 9/1988 | McFarland | 604/198 |
| 4,775,363 | 10/1988 | Sandsdalen | 604/110 |
| 4,781,684 | 11/1988 | Trenner | 604/110 |
| 4,790,827 | 12/1988 | Haber et al. | 604/198 |
| 4,790,828 | 12/1988 | Dombrowski et al. | 604/198 |
| 4,804,372 | 2/1989 | Laico et al. | 604/198 |
| 4,810,248 | 3/1989 | Masters et al. | 604/192 |
| 4,813,426 | 3/1989 | Haber et al. | 128/763 |
| 4,816,022 | 3/1989 | Poncy | 604/198 |
| 4,819,659 | 4/1989 | Sitar | 128/764 |
| 4,820,275 | 4/1989 | Haber et al. | 604/198 |
| 4,826,488 | 5/1989 | Nelson et al. | 604/192 |
| 4,826,490 | 5/1989 | Byrne et al. | 604/198 |
| 4,826,491 | 5/1989 | Schramm | 604/198 |
| 4,911,694 | 3/1990 | Dolan | 604/110 |
| 4,929,241 | 5/1990 | Kulli | 604/110 |
| 4,935,013 | 6/1990 | Haber | 604/192 |

*Primary Examiner*—C. Fred Rosenbaum
*Assistant Examiner*—Sharon Finkel
*Attorney, Agent, or Firm*—Weingarten, Schurgin, Gagnebin & Hayes

[57] ABSTRACT

A needle safety device, which is usable on long, short, straight or curved needles, is actuated to enclose the injecting end of a needle when an engagement surface of the device is slid beyond the injecting end. A unitary or multiple piece clip is provided which is slideable from a first position wherein a hypodermic needle is usable for injection purposes to a second position wherein the injecting end of the hypodermic needle is covered rendering the needle unusable and protected.

14 Claims, 4 Drawing Sheets

HYPODERMIC NEEDLE SAFETY CLIP

TECHNICAL FIELD

This invention relates to needles, particularly to a clip device for facilitating safe handling of hypodermic needles.

BACKGROUND OF THE INVENTION

Many kinds of needle protection devices are available for providing post injection needle stick protection. Needle stick protection is especially significant to health care professionals presently because of the prevalence of potentially fatal infectious diseases, such as AIDS, that can be transmitted to health care workers by inadvertent jabs from a needle subsequent to its use in an infected patient.

Common types of needle stick protection devices include sheath type protectors such as those disclosed in U.S. Pat. Nos. 4,725,267 and 4,804,371 to Vaillancourt. Sheath type protectors fully encompass the needle with a cap or end portion which may be actuated along the length of the needle to cover the sharp injecting end portion. Spring biasing may be used to effect the actuation or extension. Typically, sheath type protectors have material which extends the full length of the hypodermic needle. Provision of such amounts of material on long hypodermic needles adds considerable bulk and cost to the needle.

Another type of protective enclosure for a hypodermic needle is disclosed in U.S. Pat. No. 4,735,618 to Hagen. Hagen discloses an enclosure formed by a tubular sleeve sized for friction engagement over the barrel portion of a needle syringe. A needle guard, including a central needle channel through which the needle fits, incorporates pivotally movable arms which operate to permit the needle to pass through the central channel so as to come to rest in a needle pocket after an injection. Provision of such a needle enclosure for a large hypodermic needle would require a considerable amount of material and add bulk to the needle so as to make the needle difficult to handle. Hagen discloses an alternative embodiment which requires rivet pins and other mechanical features which may make fabrication and use of the device complex and expensive.

Similarly, U.S. Pat. No. 4,795,432 to Karczmer discloses a complex device for providing protection against inadvertent jabs by a hypodermic needle. The Karczmer device comprises various types of springs, tabs and hinged flaps required to effectuate needle stick protection. Like all the prior art discussed above, in addition to being complex, Karczmer cannot be easily adapted or modified for use on needles of various sizes and lengths.

Additionally, none of these devices would be suitable for use on curved needles used in the health care field.

SUMMARY OF THE INVENTION

In accordance with the present invention a hypodermic needle safety device is disclosed in which a unitary or multiple piece clip is provided which is slideable from a first position wherein the hypodermic needle is usable for injection purposes to a second position wherein the injecting end of the hypodermic needle is covered rendering the needle unusable and protected.

A simple needle safety device, which is usable on long, short, straight or curved needles, is actuated to enclose the injecting end of a needle when an engagement surface of the device is slid beyond the injecting end. The simple unitary or multiple piece needle safety device may be stamped from any suitable metal or injection molded from plastic to provide a low cost easily assembled safety clip.

Additional features may include the color coding of clips to correspond to particular needle sizes, the incorporation of a disinfectant medium, and the use of sufficient compressive forces to render the needle permanently non-reusable.

BRIEF DESCRIPTION OF THE DRAWING

These and other features and advantages of the present invention will become apparent in light of the detailed description of exemplary embodiments thereof, as illustrated in the accompanying drawings of which.

DETAILED DESCRIPTION OF THE INVENTION

Figure 1:
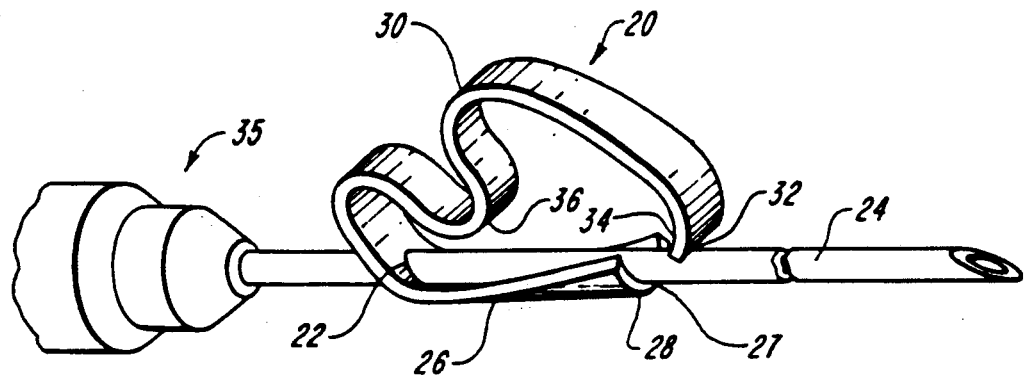
FIG. 1 is a perspective view of a unitary piece needle safety clip in a first position wherein the needle is usable.
Figure 2:
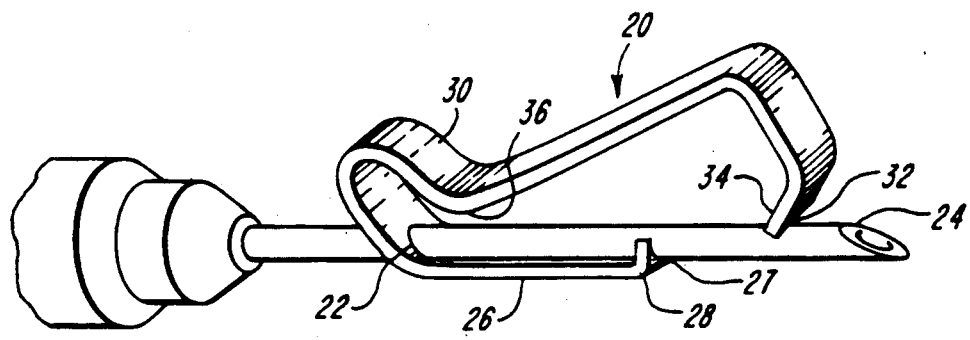
FIG. 2 is a perspective view of another embodiment of a unitary piece needle safety clip.

In one embodiment of a unitary needle safety clip, as illustrated in FIG. 1, a thin piece of metal, molded plastic or other suitable material is formed in a manner such that when it is installed on a needle, forces are directed in minimally two opposing directions, at the same time, toward a common axis defined by the needle. In the embodiments of FIGS. 1 and 2 the unitary clip 20 has a hole 22 which is sized to accommodate a hypodermic needle 24.

An alignment portion 26 of clip 20 has a slightly angled engagement surface which is substantially parallel to the hypodermic needle 24. The alignment portion engagement surface has a guide means 28 which maintains the safety clip 20 in alignment with the needle 24. Guide means 28 may be furcated as in FIG. 2, or it may be any other geometric configuration having two sides and a bottom 27, wherein the two sides are fitted to contact the periphery of the needle in order to maintain alignment. The bottom 27 of guide means 28 also contacts the periphery of the needle and exerts a force thereon.

A compression portion 30 of the clip 20 has a sliding surface 32 which contacts the periphery of the hypodermic needle 24. Sliding surface 32 exerts a force on needle 24 in a direction opposing the force exerted by the bottom 27 of guide means 28. Compression portion 30 is bent in a manner which creates opposing or transverse forces between compression portion 30 and alignment portion 26. Including bends, the compression portion is slightly longer than the alignment portion 26 such that the sliding surface 32 is closer to the injecting end of the needle 24 than the contacting portion of guide means 28. The compression portion 30 also has an abutting engagement surface 34.

Figure 3:
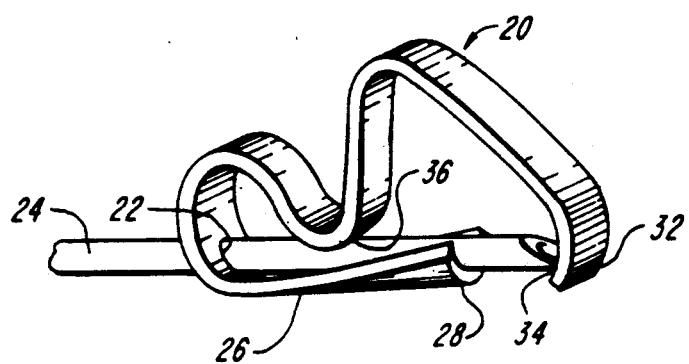
FIG. 3 is a perspective view of the needle safety clip of FIG. 1 in a second position wherein the needle is unusable and protected.

When safety clip 20 is in a first position, in which the injecting end is exposed, the clip 20 is proximate to a syringe/needle interface or hub 35 which typically comprises male/female threaded members. In this position virtually the entire length of the needle is exposed for injecting purposes. Sliding surface 32 of the compression portion 30 is in contact with the periphery of needle 24 exerting a force opposing the bottom 27 of guide means 28 which also contacts a portion of the periphery of needle 24. To activate the clip, a force is exerted at the back of clip 20, along the axis of the needle 24 and toward the injecting end. The activation force may be applied manually or by a biasing spring. The bottom 27 of guide means 28 and the sliding surface 32 of compression portion 30 each slideably engage opposed portions of the needle periphery with sliding surface 32 exerting force closer to the injecting end than the guide means 28. Hole 22 and guide means 28 keep the clip 20 in alignment with needle 24 so that sliding surface 32 is maintained in sliding engagement with needle 24. When sliding surface 32 goes beyond the injecting end or point of the needle 24 as illustrated in FIG. 3, the needle no longer counters the force exerted by the compression portion 30 and contact surface 32 is actuated downward through the axis of the needle 24. Abutting engagement surface 34 engages the injecting end in abutting relation and a friction engagement surface 36 snaps against a portion of needle 24 so as to engage the safety clip. The frictional engagement of friction engagement surface 36 and possibly hole 22 with the needle resists further slideable movement of the clip along the needle. Friction engagement surface 36 may be provided with knurling or other surface roughness so as to further increase the force required to slide the clip along the needle following engagement of the needle by the friction engagement surface 36.

Figure 4:
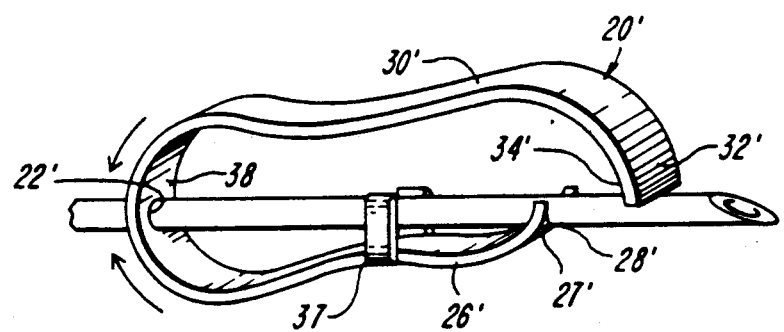
FIG. 4 is a perspective view of another embodiment of a unitary piece needle safety clip.

FIG. 4 illustrates an alternative embodiment of a unitary needle safety clip according to the invention. In this embodiment the needle clip 20' comprises alignment portion 26' having guide means 28' with bottom 27' and compression portion 30' having sliding surface 32' and abutting engagement surface 34', all of which function substantially as discussed hereinbefore with respect to FIGS. 1, 2 and 3. In this embodiment a second guide means 37 is provided. Alignment portion 26' and compression portion 30' are separated by a bent or arcuate end 38 having a hole 22' approximately centered therein. Hole 22' is of a diameter sized to be slightly larger than the outer diameter of needle 24 when sliding surface 32' and the bottom 27' of guide means 28' are separated a distance equal to the outer diameter of the needle 24. The diameter of hole 22' is sized to fit slideably on the needle 24 and is also sized such that when sliding surface 32' goes beyond the injecting end of needle 24 a deformation of hole 22' results from the actuation of contact surface 32 through the axis of needle 24. An inner surface of hole 22' effects frictional engagement of the periphery of needle 24 such that deformation of hole 22' results in grasping of needle 24 providing a high degree of frictional engagement between the clip 20' and the needle 24.

It should be appreciated by one of skill in the art, that depending on the diameter and relative strength of the needle on which a clip according to the invention is used, it may be possible to provide the compression portion 30, 30' discussed hereinbefore, or other surfaces of embodiments discussed hereinafter, with sufficient force such that actuation of the contact surface 32, 32' and engagement of the abutting surface 34, 34', or equivalents thereof, bends or otherwise deforms the injecting end of needle 24, rendering the needle 24 permanently non-reusable.

Figure 5:
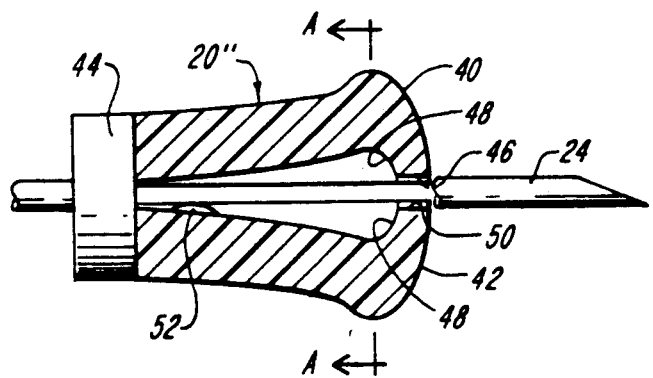
FIG. 5 is a side view, partially in section of a multiple piece needle safety clip.
Figure 5A:
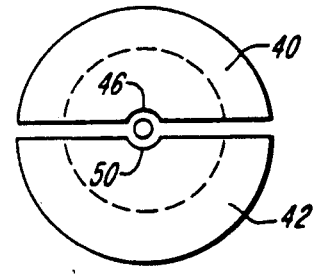
FIG. 5A is a sectional view of the needle clip of FIG. 5 taken along a line A—A.

The embodiment of FIG. 5 illustrates a unitary safety clip according to the invention having a split bushing configuration. In this embodiment the clip 20" is disposed on needle 24 by separating resilient prongs 40, 42. An end of the clip 20" opposing the end having prongs 40, 42 comprises a collar 44 fitting slideably about needle 24 while the prongs 40, 42 exert opposing forces against the needle 24. A portion of the clip 20" defining prong 40 has an arcuate surface 46 which serves as a slideable contact surface and an inner surface 48 providing an abutment surface. A portion of clip 20" defining prong 42 also has an arcuate surface 50 which serves as a guide means in slideable contact with the periphery of the needle 24 and an inner surface 48' providing an alternative abutment surface. Prong 42 further includes a frictional engagement surface 52 which, when the prongs 40, 42 are slid beyond the injecting end of needle 24, engages the periphery of needle 24 providing frictional resistance against further slideable movement of the clip 20". At that point, inner surface 48 or 48' is in abutting relation with the injecting end of needle 24. Alternatively the frictional engagement surface may be provided on prong 40 or on both prongs 40 and 42.

Figure 6:
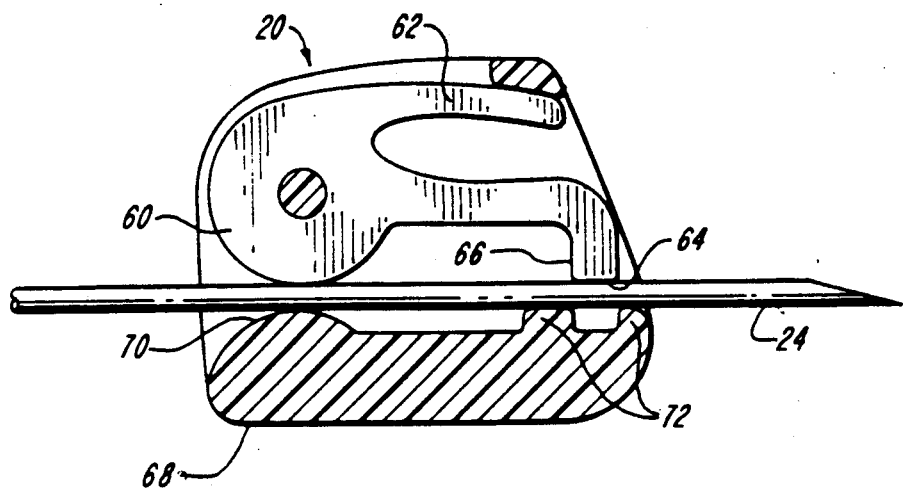
FIG. 6 is a side section view of a multiple piece needle safety clip.
Figure 7:
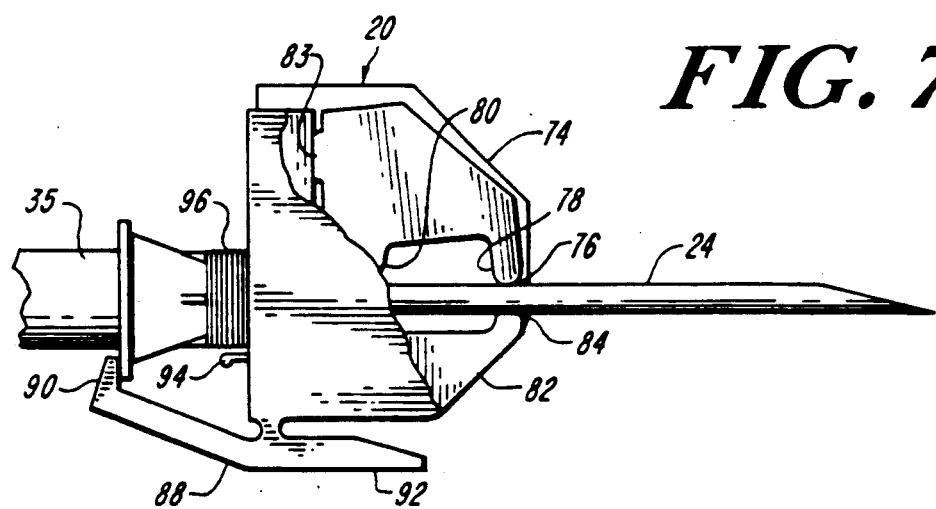
FIG. 7 is a side view partially broken away, of another multiple piece embodiment of a needle safety clip in a first position.
Figure 7A:
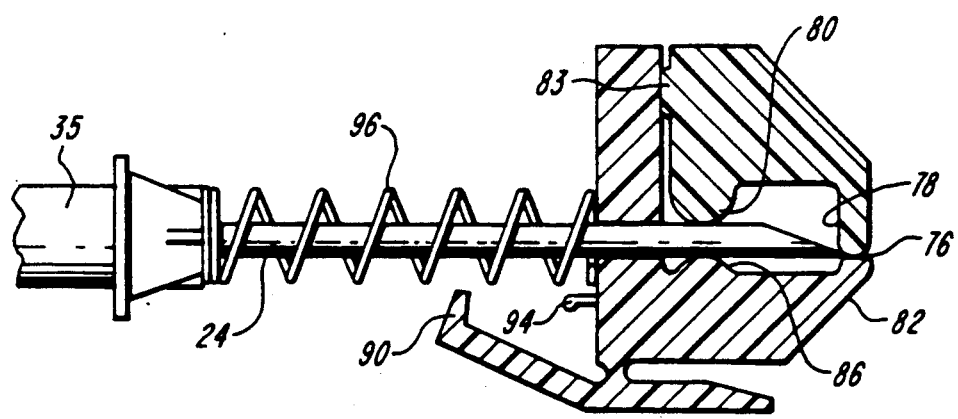
FIG. 7A is the safely clip of FIG. 7 in a second position.

Referring now to FIGS. 6, 7 and 7A, a needle safety clip is produced having multiple pieces to effect the same function and result as discussed hereinbefore with respect to FIGS. 1–5.

The embodiment of FIG. 6 comprises a clip which has a cammed piece 60 biased against needle 24 by a compressed spring portion 62. Cammed piece 60 has a slideable contact surface 64 and an internal abutting surface 66. A lower piece 68 comprises a cam opposing surface 70 and a pair of support contact surfaces 72 dimensioned to receive slideable contact surface 64 therebetween. Cammed piece 60 is mounted to a housing comprising lower piece 68, at a point which is slightly offset from the center of the arc of the cammed piece 60.

The cammed clip of FIG. 6 slideably engages the needle 24 until the contact surface 64 goes beyond the injecting end of the needle 24. At that point, compressed spring portion 62 forces contact surface 64 downward and the injecting end of the needle 24 engages internal abutting surface 66. Further actuation of the contact surface 64 beyond the injecting end of needle 24 results in contact surface 64 fitting in between support contact surfaces 72 and cammed piece 60 rotating such that the cammed piece exerts greater friction engagement against needle 24 until the needle is fully frictionally engaged. At this point the injecting end is covered protecting the user from inadvertent penetration by the needle.

The embodiment of FIGS. 7 and 7A illustrates a multiple piece needle safety clip which accommodates various sized needles. This multiple piece embodiment has a first portion 74 with a first slideable contact surface 76, an inner abutting engagement surface 78, and a first friction engagement surface 80. The first portion 74 engages a second portion 82 having a second slideable contact surface 84 and a second friction engagement surface 86. First portion 74 is mounted to second portion 82 at an interface region 83 by ultrasonic welding or other mechanical fastening means. Prior to fastening, first portion 74 is vertically adjustable so as to accommodate a needle of a predetermined size. Subsequent to fastening, first portion 74 is flexibly disposed so that the first slideable contact surface 76 normally extends below first friction engagement surface 80 when not engaging a needle. Thus, fastening of first portion 74 to second portion 82 in the above manner results in the exertion of a force by contact surface 76 on the needle 24 when the clip is disposed thereon in the first position. This embodiment illustrates an optional locking means or latch 88 which has a hook 90 that extends over the syringe/needle interface or hub 35, as known in the art, to latch the needle safety clip in the first position. Manually depressing a lever arm 92 disengages hook 90 from the hub 35 enabling activation of the clip to the second position wherein slideable contact surface 76 extends beyond the injecting end of needle 24, and is actuated through the axis of needle 24, causing the force to be exerted against the needle by the first and second friction engagement surfaces 80, 86, as illustrated in FIG. 7A. Alternatively, for syringe/needle interfaces wherein the needle hub is a male threaded member for screw insertion into a female threaded syringe (not shown) a nib 94 is provided for engagement with the female threads of such a syringe 50 that the safety clip can be rotated into locking engagement in the first position and counter-rotated to release the clip in a second position.

Further, a biasing means such as a spring 96 may be provided to assist in activating the needle safety device according to the invention from the first position to the second position.

Figure 8:
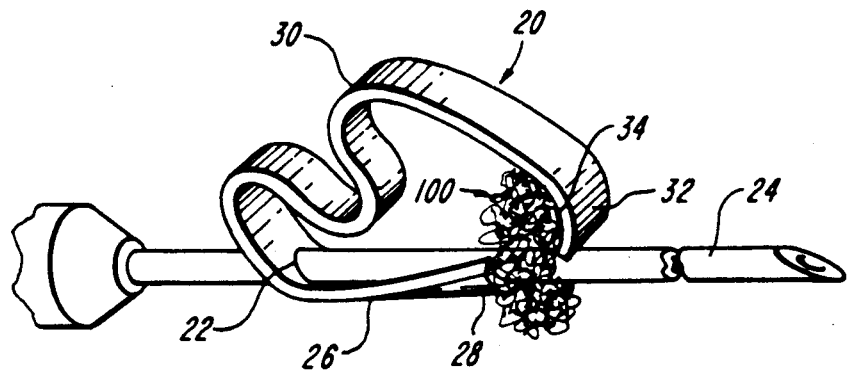
FIG. 8 is a side view of a unitary needle safety clip including an antiseptic medium and shown in a first position wherein the needle is usable.
Figure 9:
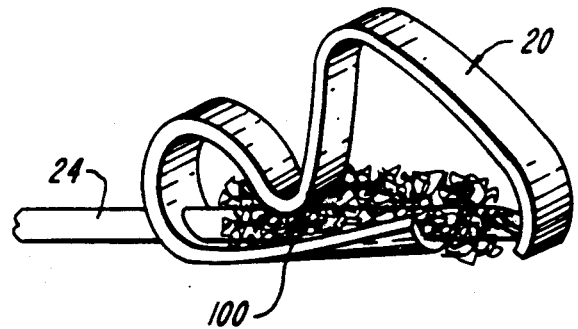
FIG. 9 is a side view of the needle clip of FIG. 8 being in a second position wherein the needle is unusable and protected.

FIGS. 8 and 9 indicate that a unitary safety clip according to the invention can be provided with an antiseptic medium 100. For example, cotton, gauze or any other suitable absorbent material may be provided with antiseptic and incorporated in the clip 20 and about the needle 24 in a manner that results in wiping of the needle by the antiseptic during slideable movement of the safety clip along the needle to the protective position. Provision of the antiseptic medium and wiping of the needle in the above described manner further enhances the safety afforded a user. An antiseptic medium can likewise be used in conjunction with other embodiments of the safety clip discussed hereinabove.

Additionally, the clips in accordance with the present invention may be color coded to indicate the size of the needle the respective clip is intended to accommodate.

Additionally, safety clips according to the invention may be variously sized and the transverse forces according to the invention may be provided by other geometric configurations. For example, the clip may be large to facilitate manual manipulation or sufficiently small so as to fit beneath commercially available needle/syringe covers.

Although the needle safety clips according to the invention have been discussed as plastic injection molded or stamped metal parts and although ultrasonic welding is discussed as a method of joining multiple piece embodiments, other materials and methods of fabrication may be used to fabricate such devices.

Although the invention has been shown and described with respect to exemplary embodiments thereof, it should be understood by those skilled in the art that the foregoing and various other changes, omissions and additions in the form and detail thereof may be made without departing from the spirit and scope of the invention.

What is claimed is:

1. A unitary safety device for use on a hypodermic needle having an injecting end, said device being slideable between a first position and a second position on said hypodermic needle, said device comprising:
   a first portion having first and second engagement surfaces, said first engagement surface being in slideable contact with the periphery of said hypodermic needle when said device is in said first position and said second engagement surface being in abutting relation with said injecting end of said hypodermic needle when said device is in said second position;
   a second portion having a third engagement surface being in slideable contact with said hypodermic needle; and
   an integral intermediate portion disposed intermediate to said first portion and said second portion, said intermediate portion having a hole, said hole being dimensioned to fit slideably about said hypodermic needle when said device is in said first position and said hole having an inner surface that frictionally engages the periphery of said hypodermic needle to grasp said hypodermic needle when said device is in said second position.

2. The hypodermic needle safety device of claim 1 further comprising a fourth engagement surface being in frictional engagement with the periphery of said hypodermic needle when said device is in said second position.

3. The hypodermic needle safety device of claim 1 wherein said injecting end of said hypodermic needle is deformed when said device is in said second position.

4. The safety device of claim 1, wherein said device is of unitary plastic construction.

5. The device of claim 1, wherein at least one of said first and said second portions further comprises a guide means for aligning said device axially with respect to said hypodermic needle.

6. The device of claim 1, further including an antiseptic medium for wiping said needle upon slideable movement of said device from said first position to said second position.

7. The device of claim 4, wherein said first engagement surface is biased toward said needle when said device is disposed in said first position and wherein said second engagement surface is actuated into abutting relation upon slideable movement of said first engagement surface to said second position.

8. The device of claim 7, wherein said first engagement surface is biased toward said needle by spring biasing caused by said first and second portions.

9. The device of claim 1, further comprising biasing means for activating said device from said first position to said second position.

10. A hypodermic needle, having a safety device, said hypodermic needle having an injection end, said device being slideable on said needle from a first injecting end exposing position to a second injection end covering position, said device comprising;
- a first member portion having a first needle engagement surface and a second injecting end protection surface;
- said first needle engagement surface being biased toward said needle when said device is in said first position and wherein said second injection end protection surface is actuated into confronting relation with said injecting end of said needle upon slideable movement of said device from said first injecting end exposing position to said second injection end covering position;
- a second member portion which is disposed adjacent to said needle when said device is in said first position and having a hole with an inner surface which frictionally engages said needle to resist slideable movement of said device with respect to said needle when said device is disposed in said second position.

11. The device of claim 10, further comprising means for aligning said clip axially with said needle.

12. The device of claim 10, further comprising an antiseptic medium for wiping said needle upon slideable movement of said device from said first position to said second position.

13. The device of claim 10, wherein said needle is deformed when said device is in said second position.

14. The device of claim 10 wherein said device is of unitary plastic construction.

* * * * *